United States Patent [19]

Fischell et al.

[11] Patent Number: 5,423,774
[45] Date of Patent: Jun. 13, 1995

[54] INTRODUCER SHEATH WITH IRREGULAR OUTER SURFACE

[75] Inventors: Robert E. Fischell, Dayton, Md.; David R. Fischell, Fair Haven, N.J.; Philip B. Fleck, Boston, Mass.

[73] Assignee: Arrow International Investment Corp., Wilmington, Del.

[21] Appl. No.: 245,149

[22] Filed: May 17, 1994

[51] Int. Cl.⁶ .................................... A61M 25/00
[52] U.S. Cl. ..................................... 604/282
[58] Field of Search ............... 604/264, 278, 280, 282; 138/130

[56] References Cited

U.S. PATENT DOCUMENTS

| | | |
|---|---|---|
| 3,428,046 | 2/1969 | Remer et al. ............ 604/278 |
| 4,368,730 | 1/1983 | Sharrock . |
| 4,955,862 | 9/1990 | Sepetka . |
| 5,069,674 | 12/1991 | Fearnot et al. . |
| 5,180,376 | 1/1993 | Fischell . |
| 5,188,152 | 2/1993 | Ogawa ...................... 138/130 |
| 5,217,482 | 6/1993 | Keith ........................ 604/282 |

FOREIGN PATENT DOCUMENTS

| | | | |
|---|---|---|---|
| 3906027 | 8/1990 | Germany | ........... 604/280 |
| 0930157 | 8/1993 | WIPO | ........... 604/264 |

Primary Examiner—C. Fred Rosenbaum
Assistant Examiner—Manuel Mendez
Attorney, Agent, or Firm—Keck, Mahin & Cate

[57] ABSTRACT

An introducer sheath for insertion into a patient's vascular system is provided having an irregular, undulating outer surface to interface with the irregular surface formed by the invasive procedure of inserting the sheath into a blood vessel. The sheath includes a helical coil member formed of continuous turns of spiral wound flat wire and a plastic sleeve surrounding the coil. Each turn of the coil is spaced apart from a next adjacent turn sufficiently to define therebetween an interstice wide enough to allow the plastic sleeve to be constricted into the interstices between the turns. A corresponding undulating outer surface is thereby formed to interface with a wall of blood vessel to minimize blood leakage therefrom. In the preferred embodiment, a lubricated inner plastic tube is proved, and a distal portion of the sheath surface has a smooth configuration.

23 Claims, 2 Drawing Sheets

INTRODUCER SHEATH WITH IRREGULAR OUTER SURFACE

BACKGROUND OF THE INVENTION

1. Field of Invention

This invention relates generally to introducer sheaths for insertion into a patient's vascular system. In particular, this invention relates to improvements to percutaneous introducer sheaths for introducing guide wires, catheters and medication into the vascular system.

2. Description of the Prior Art

An introducer sheath is used to facilitate the introduction of medical implements such as catheters, guide wires or angioplasty balloons. Typically, a needle is inserted through the patient's skin to puncture a blood vessel. The needle is then withdrawn and is replaced by an elongated pointed dilator carried within a tubular introducer sheath. Upon insertion of the introducer sheath and dilator into the blood vessel, the dilator is withdrawn and replaced by the medical implement to be used in the procedure. The introducer sheath remains in place at the entry into the blood vessel.

Prior art introducer sheaths, intravenous catheters and other catheter-like devices which are designed and intended to penetrate the walls of blood vessels are generally designed to have a smooth outer surface. The purpose of such a smooth surface is to minimize resistance encountered by the catheter or sheath as it is introduced through body tissue and into the blood vessel, and thereby reduce the force required to push the catheter through the skin and through the blood vessel wall.

Examples of prior art patents incorporating the use of a smooth, even outer surface sheath include Sepetka U.S. Pat. No. 4,955,862, Fearnot, et al, U.S. Pat. No. 5,069,674, and Fischell U.S. Pat. No. 5,180,376. Each of these prior art patents discloses the use of a smooth, plastic outer covering or tubular sheath to present a smooth outer surface. This facilitates the introduction of these sheaths into blood vessels.

While the foregoing prior art discloses intravenous catheters and introducer sheaths that may be useful and effective for a reduction of the force necessary to penetrate skin and vascular system tissue, bleeding complications around the catheter have been frequently observed. It is theorized that such bleeding complications may be caused by insufficient sealing of the catheter to the vascular wall at the point of insertion. When the sheath is forced into the vascular wall, the rupturing of the vascular tissue at the point of insertion creates an irregular tear in the vascular wall. Since a smooth outer surface catheter sheath does not mate precisely with the irregular surface of the vascular wound, little interference is provided to the leaking or oozing of blood around the sheath.

One prior art patent, Sharrock U.S. Pat. No. 4,368,730, discloses an intravenous catheter having an irregular outer surface formed by a wire-wound spring guide which surrounds the sheath body. The exposed wires present an irregular outer surface. However, the outer surface formed by the circular cross section wire may present undue resistance to easy passage of the sheath through tissue.

SUMMARY OF THE INVENTION

The present invention is designed to overcome the shortcomings of prior art introducer sheath devices by providing an irregular or undulating external surface to interact with the irregular surface of the tear at the vascular insertion point of the sheath to restrict the leaking of blood around the sheath. Specifically, the invention described herein is an introducer sheath which has an irregular exterior surface over at least part of its length. In this sense, "irregular" is meant to include undulating or uneven surfaces, whether or not such unevenness or undulation is regular or irregular in periodicity.

The present invention overcomes the shortcomings of the devices disclosed in the prior art by presenting an uneven outer surface which incorporates a smooth plastic surface with an undulating configuration. This configuration serves to reduce blood leakage around the sheath while allowing relatively facile penetration of tissue by the sheath. Further, in the preferred embodiment of the invention, the distal portion of the sheath's exterior is even and smooth to further facilitate tissue penetration.

Theoretically and experimentally, it has been determined that such irregular or undulating surfaces result in reduced leakage of blood through arterial walls around such sheaths. The interaction between the irregular torn surface of the vascular wall at the insertion wound and the irregular outer surface of the sheath serves to baffle the flow of blood past the interface between two surfaces, resulting in a more tortuous path for the escaping blood. This configuration, therefore, should and does result in reduced bleeding complications during procedures which require the insertion and retention of such catheters or sheaths.

The irregular undulating outer surface of the introducer sheath of the present invention is formed by the fitting of a thin plastic tubular member around a spaced-apart helically-wound flat wire coil. The turns of the coil are sufficiently spaced to allow the plastic outer covering to be drawn into the gaps between the turns to create an undulating outer surface. In one embodiment, wherein the distal portion of the introducer sheath is intended to have a smooth outer surface, the spaces between the coils are in that distal portion filled with plastic inserts.

Accordingly, it is an object of the present invention to provide an introducer sheath having an irregular outer surface to reduce blood leakage at the point of introducer and retention of the sheath in a blood vessel.

It is another object of the invention to provide an introducer sheath having a smoothly undulating outer surface having a periodicity of undulation sufficiently short to provide a multiplicity of undulations in contact with an irregular blood vessel surface.

It is a further object of the invention to provide an introducer sheath having a distal portion with a smooth outer surface for easy insertion through skin and vascular tissue, and a proximal irregular or undulating outer surface portion for retention at the insertion point of the vascular wall during a medical procedure, to interfere with the leakage of blood around the sheath at the insertion point.

These and other objects of the present invention will become apparent upon careful reading of the detailed description of the invention as presented herein.

DESCRIPTION OF THE PREFERRED EMBODIMENT

Figure 1:
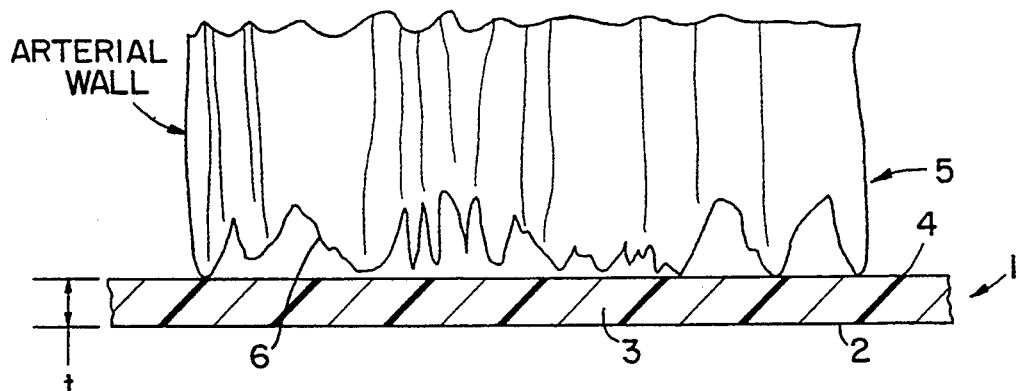
FIG. 1 (prior art) is a greatly enlarged sectional view of one wall of a prior art introducer sheath having smooth interior and exterior surfaces, with the exterior of the introducer sheath shown in contact with the surface of a vascular wound.

Referring now to the drawings, in FIG. 1 thereof there is shown a greatly enlarged cross-sectional view of one wall of a prior art introducer sheath encountering the surface of a wound in a blood vessel caused by the intrusion of the introducer sheath into the blood vessel. Arterial wall 5 is torn at irregular surface 6 in the interior of the wound. Prior art sheath 1 includes wall 3 of thickness t having smooth interior surface 2 and smooth exterior surface 4 in contact with wound surface 6 of the arterial wall. The surface irregularities at wound surface 6 are caused by the piercing of the wall and the subsequent insertion of the sheath into the artery. The irregularities of wound surface 6 do not fully correspond to the smoother outer surface 4 of wall 3 and may not provide sufficient resistance to blood leakage past the interface between the artery and sheath 1.

Figure 2:
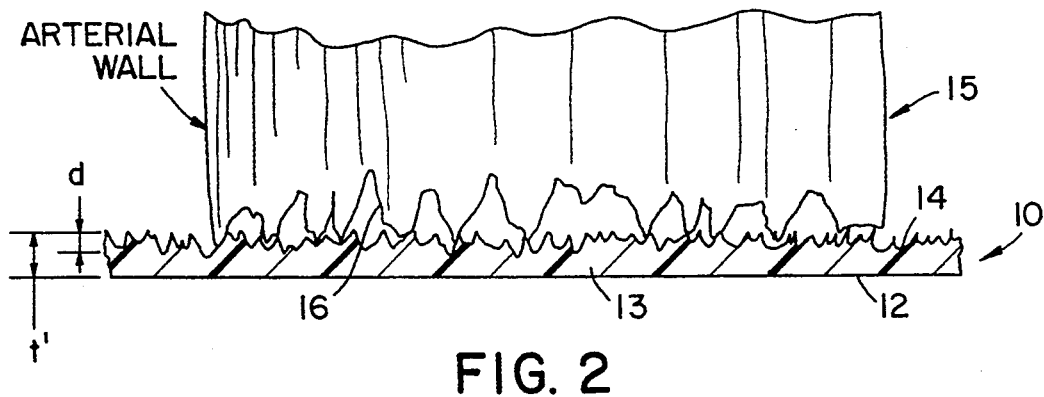
FIG. 2 is a greatly enlarged sectional view of one wall of an introducer sheath embodying the present invention having a smooth inner surface and an irregular outer surface, with the exterior of the introducer sheath shown in contact with the surface of a vascular wound.

In FIG. 2 is shown (in greatly enlarged sectional view) a portion of an introducer sheath 10 embodying the present invention. Sheath wall 13 includes smooth inner surface 12 and irregular, or roughened, outer surface 14. Irregular outer surface 14 includes an irregular array of peaks and valleys with an average depth between peak and valley of d as shown. The overall thickness of sheath wall 13 is t'. The ratio d/t' typically lies between 0.05 and 0.5.

In use, the surface irregularities of the arterial wound are displaced into the irregularities 14 of sheath 10. This interface provides impedance to the leakage of blood from the artery by impeding the flow at numerous points along its path. In this manner, a more effective seal is achieved between the sheath and the wall of the blood vessel than could be achieved by the smooth outer wall of the sheath of the prior art shown in FIG. 1. This is particularly important for reducing bleeding complications for sheaths inserted in the femoral artery at the groin. It should be noted that there is periodicity to the irregularities of either the would or the outer surface 14 of the sheath 10.

Figure 3:
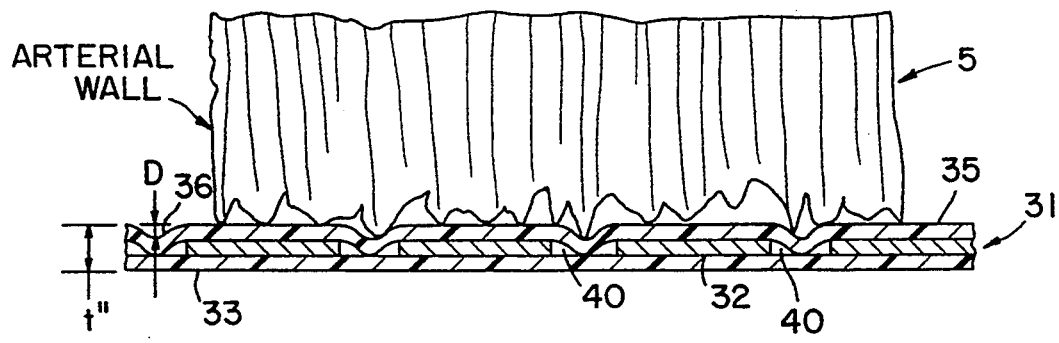
FIG. 3 is a greatly enlarged sectional view of one wall of an introducer sheath having a generally smooth inner surface and an undulating outer surface, with the exterior of the introducer sheath shown in contact with the surface of a vascular wound.
Figure 4:
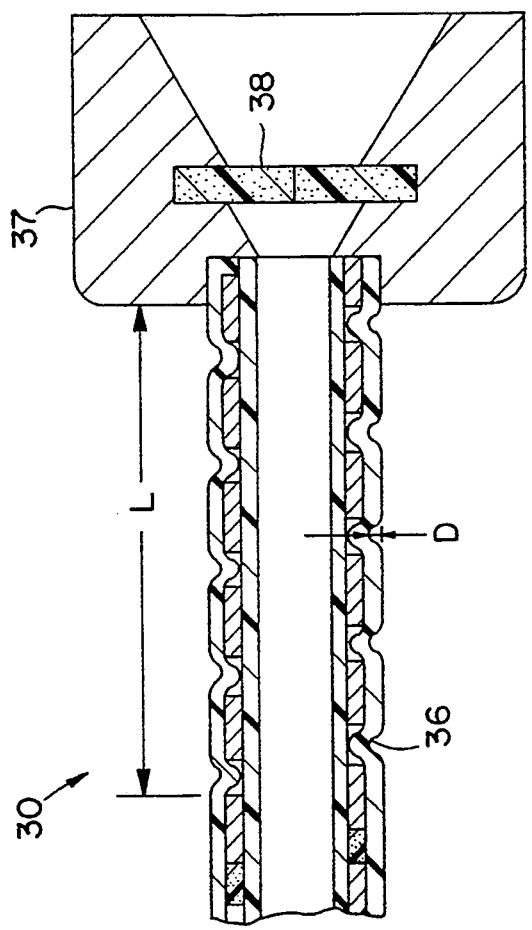
FIG. 4 is a longitudinal cross-sectional view of an introducer sheath embodying the present invention.
Figure 4:
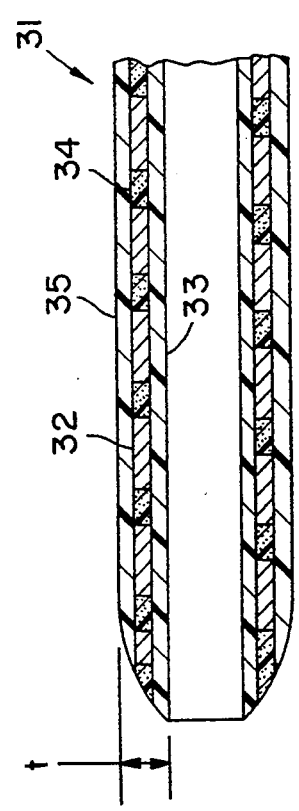

In FIGS. 3 and 4 is shown an introducer sheath which is the preferred embodiment of the present invention. FIG. 4 illustrates a longitudinal cross-sectional view of an introducer sheath 30 having an elongated, substantially tubular body 31 extending from hemostasis valve adapter 37 at the proximal end of sheath body 31 to tapered tip 39 at the distal tip of sheath body 31. Hemostasis valve adapter 37 includes hemostasis valve 38 which has slit opening 39. In use, an elongated dilator is inserted through slit opening 39 in hemostasis valve 38 and is passed through sheath body 31.

Sheath body 31 includes a flat wire helical spring coil 32 sandwiched between inner tube 33 and outer sleeve 35. Sheath body 31 can be created by overextruding or heat-shrinking a plastic tube over helical coil member 32 which has been wound over inner plastic tube 33 which, in turn, has been extruded over and retained on a mandrel. A detailed description of the construction of a similar introducer sheath design is contained in Fischell, U.S. Pat. No. 5,180,376, entitled "Non-Buckling Thin-walled Sheath for the Percutaneous Insertion of Intraluminal Catheters." The outer surface of the introducer sheath disclosed in Fischell '376 is substantially smooth due to the close spacing of the adjacent turns of the flat wire coil in that introducer sheath, and does not incorporate the undulating outer surface of the present invention.

Helical coil 32 would typically be fabricated from 300 series stainless steel. The thickness of helical coil 32 typically lies in the range between 0.02 and 0.2 mm, and the width of the wire would typically be between 5 and 50 times the wire thickness. The inner diameter of the helical coil would typically lie between 1 and 5 mm depending on the size of the catheter that is to be inserted through it.

The plastic material of these introducer sheaths or catheters is typically polyethylene, polyurethane, PVC, teflon or an equivalent plastic material. The hemostasis valve 38 is typically formed from silicone rubber. The inner tube 33 may be fabricated with an inner surface coating of PTFE to allow for easier insertion of the elongated dilator, guide wire, or catheter.

In this embodiment, adjacent turns of coil 32 are spaced between 0.5 and 5 mm; i.e., sufficient to define interstices 40 therebetween.

In the process of heat shrinking plastic sleeve 35 around helical coil 32, sleeve 35 is drawn into interstices 40, thereby defining indentations 36 in the outer surface of outer sleeve 35 of sheath 31. Adjacent turns of coil 34 are sufficiently spaced apart to allow full constriction of outer sleeve 35 to form indentations 36 and to thereby present an uneven outer sheath surface. Indentations 36 have a typical depth D between 0.5 and 1.0 times the thickness of the flat wire of coil 34. The distance from the midpoint of one indentation to the next is equal to the width of the flat wire used plus the width of the gap between the turns of wire. The ratio D/t typically lies between 0.05 and 0.5.

In the preferred embodiment of the present invention, as shown in FIG. 4, both undulating and smooth outer surfaces are provided on the introducer sheath. For a length "L" (typically 3 to 7 cm) from the hemostasis valve adapter 37 along the proximal length of the sheath, the sheath body has an undulating outer surface. As previously described, the undulating surface is formed by the spiral constriction of the outer sleeve into interstices 40 between turns of the flat wire coil 32. For the remaining length of sheath 31, to its distal end 39, the outer covering of the sheath is smooth and even to allow for facile passage of the sheath through the patient's skin and into and through the arterial wall. This even surface is developed by the positioning of a plastic spacer 34 in interstices 40 from the end of segment L to the distal tip 39 of the sheath. This design has the advantage of a smooth outer surface for most of its length for easier passage through the skin and blood vessel wall, and an undulating or irregular proximal surface where the sheath is retained in position through the wall of the blood vessel. As can be seen in FIG. 3, when insertion is effected, an irregular arterial wall side surface is created at the site of the wound. The irregular side surface vessel wall is displaced into valleys 36 of undulating surface 35 in section L. In this manner blood leakage at the insertion point is inhibited.

While the description of the invention has been in connection with preferred embodiments, it will be understood that it is not intended to limit the invention thereto, but it is intended to cover all modifications and alternative constructions falling within the spirit and scope of the invention as expressed in the appended claims.

What is claimed is:

1. A sheath for introduction of a medical implement into a blood vessel of a living body, said sheath including:
   a helical coil member formed of continuous turns of spiral wound flat wire and a plastic sleeve surrounding said coil and contiguously located adjacent thereto, extending substantially the insertable length of said helical coil member;
   wherein each turn of said coil is spaced apart from a next adjacent turn sufficiently to define therebetween an interstice wide enough to allow said plastic sleeve to be drawn into said interstice upon constriction to define a corresponding undulating outer surface of said sleeve at a region of contact with the blood vessel for contiguously interfacing with a wall of said vessel and minimizing blood leakage therefrom.

2. An introducer sheath as in claim 1 further including an inner thin-walled elastomer member contiguously located adjacent an inner surface of said flat wire helical coil member.

3. An introducer sheath as in claim 2 wherein said inner thin walled elastomer member is a plastic tube extending substantially throughout the length of said flat wire helical coil member.

4. An introducer sheath as in claim 3 wherein said plastic tube includes a lubricating coating formed on an interior surface thereof.

5. An introducer sheath as in claim 4 wherein said lubricating coating comprises PTFE.

6. An introducer sheath as in claim 1 wherein a distal portion of the length of said sheath includes a spacer filling the interstices of the adjacent turns of said coil to prevent the constriction of said plastic sleeve into said interstices so as to define a corresponding smooth outer surface over said distal portion of the sheath to reduce force required to insert that portion of the sheath into and through body tissue.

7. A sheath according to claim 1, wherein the helical coil member has an inner surface that forms an introducer lumen.

8. A sheath according to claim 1 wherein the interstice has a width in the range from about 0.5 mm to about 5 mm.

9. A sheath for introduction of a medical implement into a blood vessel of a living body, said sheath including:
   a helical coil member formed of continuous turns of spiral wound wire and a plastic sleeve surrounding said coil and contiguously located adjacent thereto, extending substantially the insertable length of said helical coil member;
   wherein each turn of said coil is spaced apart from a next adjacent turn sufficiently to define therebetween an interstice wide enough to allow said plastic sleeve to be drawn into said interstice upon constriction to define a corresponding undulating outer surface of said sleeve at a region of contact with the blood vessel for contiguously interfacing with a wall of said vessel and minimizing blood leakage there from.

10. An introducer sheath as in claim 9 wherein said wire is of flat cross-section to minimize the outer dimension of said introducer sheath.

11. An introducer sheath as in claim 10 wherein said plastic sleeve has an outer surface which is constricted into said interstices to a depth of between 0.5 and 1.0 times the thickness of the flat wire.

12. An introducer sheath as in claim 10 wherein said sheath has an inner surface and an outer surface, and the ratio of the depth of said constriction to the thickness of the sheath between said inner surface and said outer surface is between 0.05 and 0.5.

13. A sheath claim 9, wherein the helical coil member has an inner surface that forms an introducer lumen.

14. A sheath according to claim 9, wherein the interstice has a width in a range from about 0.5 mm to about 5 mm.

15. A sheath for introduction of a medical implement into a blood vessel of a living body, said sheath including:
   an elongated tubular body defining an introducer lumen therein and having a proximal longitudinal region and a distal longitudinal region;
   said proximal region having an irregular outer surface for contingously interfacing with a wall of the vessel to minimize blood leakage, and said distal region having a smooth outer surface.

16. The sheath as in claim 15, wherein said proximal region is less than half of the total length of the sheath.

17. The sheath as in claim 15, wherein said proximal region is less than 10 cm.

18. The sheath as in claim 15 wherein said sheath includes a helical coil member formed of continuous turns of spiral wound wire and a plastic sleeve surrounding said coil and contiguously located adjacent thereto; and
   wherein each turn of said coil is spaced apart from a next adjacent turn sufficiently to define therebetween an interstice wide enough to allow said plastic sleeve to be drawn into said interstice in said proximal region upon constriction to define a corresponding undulating outer surface of said sleeve in said proximal region for contiguously interfacing with a wall of said vessel and minimizing blood leakage therefrom; said sheath including
   at least one spacer located in said interstice in said distal region to prevent constriction of said plastic sleeve so as to define a smooth outer surface in said distal region.

19. An introducer sheath as in claim 18 wherein said wire is of flat cross-section.

20. A sheath for introducing a medical implement into a blood vessel comprising:
   a helical coil having a plurality of turns spaced apart from one another to define an interstice therebetween; and
   a plastic sleeve extending substantially the insertable length of the sheath, and having a distal region having a smooth outer surface and a proximal region having an irregular outer surface for contiguously interfacing with a wall of said vessel and minimizing blood leakage.

21. A sheath according to claim 20, wherein the helical coil has an inner surface that forms an introducer lumen.

22. A sheath according to claim 20, wherein the interstice has a width in a range from about 0.5 mm to about 5 mm.

23. A method for introducing a medical implement into the lumen of a blood vessel of a living body with an introducer sheath, said method including the steps of:

puncturing a blood vessel at a point of insertion;

inserting into said blood vessel at said point of insertion an elongated dilator and a substantially tubular introducer sheath surrounding said dilator, said introducer sheath having an introducer lumen, a distal portion with a smooth outer surface and a proximal portion with an irregular outer surface;

passing said introducer sheath into said blood vessel until said irregular surface is in contact with the wall of said blood vessel;

retaining said irregular surface in contact with said blood vessel wall at said point of insertion to impede the leakage of blood from said blood vessel around said sheath;

removing said dilator; and inserting said catheter or the like through said introducer sheath and into said blood vessel.

* * * * *